United States Patent
Nair et al.

(10) Patent No.: US 6,548,719 B1
(45) Date of Patent: Apr. 15, 2003

(54) PROCESS FOR PRODUCING FLUOROOLEFINS

(75) Inventors: Haridasan K. Nair, Williamsville, NY (US); Michael Van Der Puy, Amherst, NY (US); David Nalewajek, West Seneca, NY (US); Timothy R. Demmin, Grand Island, NY (US); Andrew J. Poss, Kenmore, NY (US); David E. Bradley, Buffalo, NY (US); Ian R. Shankland, Randolph, NJ (US)

(73) Assignee: Honeywell International, Morristown, NJ (US)

( * ) Notice: Subject to any disclaimer, the term of this patent is extended or adjusted under 35 U.S.C. 154(b) by 0 days.

(21) Appl. No.: 09/962,974

(22) Filed: Sep. 25, 2001

(51) Int. Cl.$^7$ ............................................... C07C 17/25
(52) U.S. Cl. ........................................................ 570/157
(58) Field of Search ......................................... 570/157

(56) References Cited

U.S. PATENT DOCUMENTS

| | | | |
|---|---|---|---|
| 2,889,379 | A | 6/1959 | Ruh et al. |
| 4,465,786 | A | 8/1984 | Zimmer et al. |
| 4,798,818 | A | 1/1989 | Baizer et al. |
| 5,532,419 | A | 7/1996 | Van Der Puy et al. |
| 5,710,352 | A | 1/1998 | Tung |
| 5,728,904 | A | 3/1998 | Van Der Puy et al. |
| 5,969,198 | A | 10/1999 | Thenappan et al. |
| 6,023,004 | A | 2/2000 | Thenappan et al. |
| 6,380,446 | B1 * | 4/2002 | Drew et al. |

FOREIGN PATENT DOCUMENTS

EP    0 974 571 A2    1/2000

OTHER PUBLICATIONS

Kimura, Yoshikazu and Regen, Steven L., Poly(ethylene glycols) and Poly(ethylene glycol)–Grafted Copolymers Are Extraordinary Catalysts for Dehydrohalogenation under Two–Phase and Three–Phase Conditions, J. Org. Chem, 1983, pp. 195–198.

Halpern, Marc, Zahalka, Hayder, Sasson, Yoel, and Rabinovitz, Mordecai, Hydroxide Initiated Reactions Under Phase Transfer Catalysis Conditions. 9. Dehydrohalogenation of (Haloethyl)benzenes by Quaternary Ammonium Salts, J. Org. Chem., 1985, pp. 5088–5092.

Henne, Albert and Waalkers, T. Phillip, Fluorinated Derivatives of Propane and Proylene, J. Am. Chem. Soc., 1946, pp. 496–497, 68.

Tarrant, Paul, Lovelance, Alan M., and Lilyquist, Marvin R., Free Radical Additions Involving Fluorine Compounds. IV. The Addition of Dibromodifluoromethane to Some Fluoroolefins, J. Am. Chem. Soc., 1955, pp. 2783–2787, 77.

* cited by examiner

*Primary Examiner*—Alan Siegel
(74) *Attorney, Agent, or Firm*—Colleen Szuch; Deborah M. Chess

(57) ABSTRACT

A process for producing a fluoroolefin of the formula: $CF_3CY=CX_nH_p$ wherein Y is a hydrogen atom or a halogen atom (i.e., fluorine, chlorine, bromine or iodine); X is a hydrogen atom or a halogen atom (i.e., fluorine, chlorine, bromine or iodine); n and p are integers independently equal to 0, 1 or 2, provided that (n+p)=2; comprising contacting, in the presence of a phase transfer catalyst, a compound of the formula: $CF_3C(R^1_aR^2_b)C(R^3_cR^4_d)$, wherein $R^1$, $R^2$, $R^3$, and $R^4$ are independently a hydrogen atom or a halogen selected from the group consisting of fluorine, chlorine, bromine and iodine, provided that at least one of $R^1$, $R^2$, $R^3$, and $R^4$ is halogen and there is at least one hydrogen and one halogen on adjacent carbon atoms; a and b are independently=0, 1 or 2 and (a+b)=2; and c and d are independently=0, 1, 2 or 3 and (c+d)=3; and at least one alkali metal hydroxide. The alkali metal hydroxide can be, for example, potassium or sodium hydroxide and the phase transfer catalyst can be, for example, at least one: crown ether such as 18-crown-6 and 15-crown-5; or onium salt such as, quaternary phosphonium salt and quaternary ammonium salt. The olefin is useful, for example, as an intermediate for producing other industrial chemicals and as a monomer for producing oligomers and polymers.

17 Claims, No Drawings

PROCESS FOR PRODUCING FLUOROOLEFINS

BACKGROUND OF THE INVENTION

The present invention relates to a process for producing fluoroolefins or fluorohaloolefins or fluorine-containing olefins, sometimes referred to hereinafter for convenience as fluoroolefins or fluorine-containing olefins, useful as intermediates for making industrial chemicals, in good yield, on an industrial scale and using commercially and readily available starting materials. More particularly, the present invention relates to a process for producing fluoroolefins, for example, 1,1,1,3,3-pentafluoropropene (also designated as "HFC-1225zc"), by the dehydrohalogenation of a halofluorocarbon, for example, 1-chloro-1,1,3,3,3-pentafluoropropane (also designated as "HCFC-235fa") which halofluorocarbon can be produced by photochlorinating 1,1,3,3,3-pentafluoropropane (also designated as "HFC-245fa").

The production of fluoroolefins such as $CF_3CH=CH_2$ by catalytic vapor phase fluorination of various saturated and unsaturated halogen-containing $C_3$ compounds is described in U.S. Pat. Nos. 2,889,379; 4,798,818; and 4,465,786.

U.S. Pat. No. 5,532,419 discloses a vapor phase catalytic process for the preparation of fluorinated olefins using a chloro- or bromo-halofluorocarbon and HF.

EP 974571 discloses the preparation of 1,1,1,3-tetrafluoropropene by contacting 1,1,1,3,3-pentafluoropropane (HFC-245fa) with either an aqueous or alcoholic solution of KOH, NaOH, $Ca(OH)_2$ or $Mg(OH)_2$ or by contact of the HFC-245fa in the vapor phase with a chromium based catalyst at elevated temperature.

A. L. Henne et al., J.Am.Chem.Soc. (1946) 68, 496–497, describe the synthesis of various fluoroolefins from $CF_3CH_2CF_3$ using, e.g., alcoholic KOH, with varying degrees of success. For example, it is stated that in some instances dehydrochlorination was unsuccessful, in another instance a protracted reaction time (three days) was required, or relatively low product yield (40%, 65%) was obtained.

P. Tarrant et al., J.Am.Chem.Soc. (1955), 77, 2783–2786, describe the synthesis of $CF_3CH=CF_2$ starting with: (1) 3-bromo-1,1,1,3,3-pentafluoropropane and reacting it with a hot solution of potassium hydroxide in water; and (2) 3-bromo-1,1,3,3-tetrafluoropropene and reacting it with HF at 150° C. and neutralizing the reaction products with a potassium hydroxide solution.

Y. Kimura et al., J.Org.Chem. (1983), 48, 195–198, describe multiphase dehydrohalogenation of brominated compounds using aqueous potassium hydroxide and a phase transfer catalyst based on polyethylene glycols and polyethylene glycol-grafted copolymers. The authors note that poor results were obtained in the case of dehydrochlorination (page 197) and that $C_8$ and $C_{10}$ polyglycols having terminal hydroxyl groups were particularly effective compared to other phase transfer catalysts such as tetraalkylammonium salts, benzyltriethylammonium chloride and crown ethers. The authors also describe the selective activity for various phase transfer catalysts in particular reactions.

M. Halpern et al., J.Org.Chem. (1985), 50, 5088–5092, describe hydroxide ion (aqueous sodium hydroxide) initiated elimination of HCl and HBr from haloaromatic compounds using a quaternary ammonium salt phase transfer catalyst.

In view of the limited technology available to do so, it was desirable to develop an efficient, industrially acceptable method for producing fluoroolefins.

SUMMARY OF THE INVENTION

Process for the preparation of a fluoroolefin of the formula $CF_3CY=CX_nH_p$ wherein Y is a hydrogen atom or a halogen atom selected from the group consisting of fluorine, chlorine, bromine or iodine; X is a hydrogen atom or a halogen atom selected from the group consisting of fluorine, chlorine, bromine or iodine; n and p are integers independently equal to 0, 1 or 2, provided that (n+p)=2 comprising contacting, in the presence of a phase transfer catalyst: (A) a compound of the formula $CF_3C\ (R^1_aR^2_b)C(R^3_cR^4_d)$ wherein $R^1$, $R^2$, $R^3$, and $R^4$ are independently a hydrogen atom or a halogen selected from the group consisting of fluorine, chlorine, bromine and iodine, provided that at least one of $R^1$, $R^2$, $R^3$, and $R^4$ is halogen and there is at least one hydrogen and one halogen on adjacent carbon atoms; a and b are independently=0, 1 or 2 and (a+b)=2; and c and d are independently=0, 1, 2 or 3 and (c+d)=3; and (B) at least one alkali metal hydroxide. The compound of step (A) can be $CF_3CH_2CF_2H$ (a commercially available compound also known as HFC-245fa) or $CF_3CH_2CF_2Cl$, a by-product from the manufacture of HFC-245fa.

DETAILED DESCRIPTION

The present invention can be generally described as a process for the preparation of fluoroolefins of the formula $CF_3CY=CX_nH_p$ wherein Y is a hydrogen atom or a halogen atom selected from the group consisting of fluorine, chlorine, bromine or iodine; X is a hydrogen atom or a halogen atom selected from the group consisting of fluorine, chlorine, bromine or iodine; n and p are integers independently equal to 0, 1 or 2, provided that (n+p)=2, comprising contacting, in the presence of a phase transfer catalyst: (A) a compound of the formula $CF_3C\ (R^1_aR^2_b)C(R^3_cR^4_d)$ wherein $R^1$, $R^2$, $R^3$, and $R^4$ are independently a hydrogen atom or a halogen selected from the group consisting of fluorine, chlorine, bromine and iodine, provided that at least one of $R^1$, $R^2$, $R^3$, and $R^4$ is halogen; a and b are independently=0, 1 or 2 and (a+b)=2; and c and d are independently=0, 1, 2 or 3 and (c+d)=3; and (B) at least one alkali metal hydroxide.

Fluoroolefins are produced by the process of the present invention by dehydrohalogenating, in the presence of a phase transfer catalyst, a compound of formula (I) comprising contacting the compound of formula (I) with at least one alkali metal hydroxide:

$$CF_3C(R^1_aR^2_b)C(R^3_cR^4_d) \qquad (I)$$

wherein $R^1$, $R^2$, $R^3$, and $R^4$ are independently a hydrogen atom or a halogen selected from the group consisting of fluorine, chlorine, bromine and iodine, provided that at least one of $R^1$, $R^2$, $R^3$, and $R^4$ is halogen and there is at least one hydrogen and one halogen on adjacent carbon atoms; a and b are independently=0, 1 or 2 and (a+b)=2; and c and d are independently=0, 1, 2 or 3 and (c+d)=3. Included among the compounds of formula (I) that can be used in the present invention is 1,1,1,3,3-pentafluoropropane or HFC-245fa. Various methods for producing this material are described in U.S. Pat. Nos. 5,710,352; 5,969,198; and 6,023,004. Another method described in U.S. Pat. No. 5,728,904 is said to be economical, amenable to large scale application and uses readily available raw materials. The process of that patent uses three steps, as follows: 1) formation of $CCl_3CH_2CCl_3$ by the reaction of $CCl_4$ with vinylidene chloride; 2) conversion of $CCl_3CH_2CCl_3$ to $CF_3CH_2CF_2Cl$ by reaction with HF in the presence of a fluorination catalyst, selected from $TiCl_4$, $SnCl_4$ or mixtures thereof; and 3) reduction of $CF_3CH_2CF_2Cl$ to $CF_3CH_2CF_2H$. Since both $CF_3CH_2CF_2H$ and $CF_3CH_2CF_2Cl$ are useful in the present invention for producing a fluoroolefin, the described process can be utilized to obtain alternative starting materials. Furthermore, commercial quantities of $CF_3CH_2CF_2H$, also known as HFC-245fa, are available from Honeywell International Inc., Morristown, N.J. for use as the starting material of the present process for direct conversion to the olefin $CF_3CH=CFH$ by dehydrofluorination according to the process disclosed herein. Other useful starting materials for the production of fluoroolefins and/or fluorohaloolefins include the following: $CF_3CH_2CF_2Br$; $CF_3CH_2CF_2I$; $CF_3CHFCF_2Br$; $CF_3CH_2CH_2Cl$; $CF_3CH_2CH_2Br$; $CF_3CH_2CH_2I$; $CF_3CHBrCF_2Br$; $CF_3CHClCF_2Cl$; $CF_3CH_2CFHCl$; $CF_3CH_2CFHBr$; $CF_3CHClCF_2H$; $CF_3CH_2CCl_3$; $CF_3CH_2CF_3$; and the like.

In order to carry out the dehydrohalogenation process step of the present invention there is employed at least one alkali metal hydroxide. The alkali metal is selected from the group consisting of the metals of Group 1 of the Periodic Table of the Elements as shown in Hawley's Condensed Chemical Dictionary, 13$^{th}$ Edition, 1997. Reference to "groups" in this table is made according to the "New Notation". Preferably the alkali metal is selected from the group consisting of lithium, sodium and potassium; more preferably, sodium and potassium; most preferably, potassium. Useful concentrations of the hydroxide are from about 1 to about 50 wt. %; preferably from about 5 to about 30 wt. %; most preferably from about 10 to about 30 wt. %. While it is possible to use hydroxides other than alkali metal hydroxides, they tend to be less soluble, particular in aqueous systems and are therefore less desirable. For example, hydroxides of the Group 2 metals (e.g., Ca, Mg, and Ba) are of this type; such as magnesium hydroxide. In carrying out the process, the molar ratio of hydroxide, preferably alkali metal hydroxide, relative to the amount of $CF_3C(R^1_aR^2_b)C(R^3_cR^4_d)$ is from about 1 to about 20; preferably from about 1 to about 15; more preferably from about 1 to about 12; for example, from about 1 to about 10.

The dehydrohalogenation reaction can be accomplished using an aqueous solution of at least one alkali metal hydroxide, without the need for additional solvent or diluent, other than the water present as a consequence of using aqueous base or alkali metal hydroxide. However, a solvent or diluent can be used if desired for convenience in carrying out the process, e.g., to modify the system viscosity, to act as a preferred phase for reaction by-products, or to increase thermal mass, etc. Useful solvents or diluents include those that are not reactive with or negatively impact the equilibrium or kinetics of the process and include alcohols such as methanol and ethanol; ethers such as diethyl ether, dibutyl ether; esters such as methyl acetate, ethyl acetate and the like; linear, branched and cyclic alkanes such as cyclohexane, methylcyclohexane; fluorinated diluents such as perfluoroisopropanol, perfluorotetrahydrofuran; chlorofluorocarbons such as $CFCl_2CF_2Cl$, etc.

The dehydrohalogenation reaction is conveniently and preferably conducted in the presence of a phase transfer catalyst. For purposes of the present invention, a phase transfer catalyst is a substance that facilitates the transfer of ionic compounds (e.g., reactants or components) into an organic phase from, e.g., a water phase. In the present invention, an aqueous or inorganic phase is present as a consequence of the alkali metal hydroxide and an organic phase is present as a result of the fluorocarbon. The phase transfer catalyst facilitates the reaction of these dissimilar and incompatible components. While various phase transfer catalysts may function in different ways, their mechanism of action is not determinative of their utility in the present invention provided that the phase transfer catalyst facilitates the dehydrohalogenation reaction based on the identified reactants. The phase transfer catalyst can be ionic or neutral and is selected from the group consisting of crown ethers, onium salts, cryptates and polyalkylene glycols and derivatives thereof. An effective amount of the phase transfer catalyst should be used in order to effect the desired reaction; such an amount can be determined by limited experimentation once the reactants, process conditions and phase transfer catalyst are selected. Typically, the amount of catalyst used relative to the amount of $CF_3C(R^1_aR^2_b)C(R^3_cR^4_d)$ present is from about 0.001 to about 10 mol %; for example from about 0.01 to about 5 mol %; alternatively, for example from about 0.05 to about 5 mol %

Crown ethers are cyclic molecules in which ether groups are connected by dimethylene linkages; the compounds form a molecular structure that is believed to be capable of "receiving" or holding the alkali metal ion of the hydroxide and to thereby facilitate the reaction. Particularly useful crown ethers include 18-crown-6, especially in combination with potassium hydroxide; 15-crown-5, especially in combination with sodium hydroxide; 12-crown-4, especially in combination with lithium hydroxide. Derivatives of the above crown ethers are also useful, e.g., dibenzo-18-crown-6, dicyclohexano-18-crown-6, and dibenzo-24-crown-8 as well as 12-crown-4. Other polyethers particularly useful for alkali metal compounds, and especially for lithium, are described in U.S. Pat. No. 4,560,759 which is incorporated herein by reference to the extent permitted. Other compounds analogous to the crown ethers and useful for the same purpose are compounds which differ by the replacement of one or more of the oxygen atoms by other kinds of donor atoms, particularly N or S, such as hexamethyl-[14]-4,11-dieneN$_4$.

Onium salts include quaternary phosphonium salts and quaternary ammonium salts that may be used as the phase transfer catalyst in the process of the present invention; such compounds can be represented by the following formulas II and III:

 (II)

 (III)

wherein each of $R^1$, $R^2$, $R^3$ and $R^4$, which may be the same or different, is an alkyl group, an aryl group or an aralkyl group, and X' is a halogen atom. Specific examples of these compounds include tetramethylammonium chloride, tetramethylammonium bromide, benzyltriethylammonium chloride, methyltrioctylammonium chloride (available commercially under the brands Aliquat 336 and Adogen 464), tetra-n-butylammonium chloride, tetra-n-butylammonium bromide, tetra-n-butylammonium hydrogen sulfate, tetra-n-butylphosphonium chloride, tetraphenylphosphonium bromide, tetraphenylphosphonium chloride, triphenylmethylphosphonium bromide and triphenylmethylphosphonium chloride. Among them, benzyltriethylammonium chloride is preferred for use under strongly basic conditions. Other useful compounds within this class of compounds include those exhibiting high temperature stabilities (e.g., up to about 200° C.) and including 4-dialkylaminopyridinium salts such as tetraphenylarsonium chloride, bis[tris(dimethylamino)phosphine]iminium chloride and tetratris[tris(dimethylamino)phosphinimino]phosphonium chloride; the latter two compounds are also reported to be stable in the presence of hot, concentrated sodium hydroxide and, therefore, can be particularly useful.

Polyalkylene glycol compounds useful as phase transfer catalysts can be represented by the formula:

$$R^6O(R^5O)_tR^7 \quad (IV)$$

wherein $R^5$ is an alkylene group, each of $R^6$ and $R^7$, which may be the same or different, is a hydrogen atom, an alkyl group, an aryl group or, an aralkyl group, and t is an integer of at least 2. Such compounds include, for example glycols such as diethylene glycol, triethylenre glycol, tetraethylene glycol, pentaethylene glycol, hexaethylene glycol, diisopropylene glycol, dipropylene glycol, tripropylene glycol, tetrapropylene glycol and tetramethylene glycol, and monoalkyl ethers such as monomethyl, monoethyl, monopropyl and monobutyl ethers of such glycols, dialkyl ethers such as tetraethylene glycol dimethyl ether and pentaethylene glycol dimethyl ether, phenyl ethers, benzyl ethers, and polyalkylene glycols such as polyethylene glycol (average molecular weight about 300) dimethyl ether, polyethylene glycol (average molecular weight about 300) dibutyl ether, and polyethylene glycol (average molecular weight about 400) dimethyl ether. Among them, compounds wherein both $R^6$ and $R^7$ are alkyl groups, aryl groups or aralkyl groups are preferred.

Cryptates are another class of compounds useful in the present as phase transfer catalysts. These are three-dimensional polymacrocyclic chelating agents that are formed by joining bridgehead structures with chains that contain properly spaced donor atoms. For example, bicyclic molecules that result from joining nitrogen bridgeheads with chains of (—OCH2CH2—) groups as in 2.2.2-cryptate (4,7,13,16,21,24-hexaoxa-1,10-diasabicyclo-(8.8.8) hexacosane; available under the brand names ryptand 222 and Kryptofix 222). The donor atoms of the bridges may all be O, N, or S, or the compounds may be mixed donor macrocycles in which the bridge strands contain combinations of such donor atoms.

Combinations of phase transfer catalysts from within one of the groups described above may also be useful as well as combinations or mixtures from more than one group, for example, crown ethers and oniums, or from more than two of the groups, e.g., quaternary phosphonium salts and quaternary ammonium salts, and crown ethers and polyalkylene glycols.

The reaction is conducted usually at a temperature within the range of from about 0° C. or slightly above to about 80° C., preferably from about 0° C. or slightly above to about 60° C., more preferably from about 0° C. or slightly above to about 40° C.; for example from about 0° C. to about 25° C. Reference to "slightly above" is intended to mean in the range of from about 1 to about 5° C. and temperatures therein between. Under process conditions where freezing of the diluent, solvent or reactants is not a factor, temperatures below 0° C. can be used, for example from about –20° C. to about 80° C.; preferably from about –10° C. to about 60° C.; more preferably from about –5° C. to about 40° C.

While there is no particular restriction as to the reaction pressure, in other words the reaction may be conducted under atmospheric pressure or under an elevated pressure, it may be necessary to operate at elevated pressure if it is desired to maintain the fluorocarbon starting material and the fluoroolefin in the liquid state, at least during the reaction. When the reaction is conducted under elevated pressure, useful pressures are from about 1 to about 5 atmospheres (about 100 kPa to about 500 kPa). The reaction time can vary in accordance with the starting compound $CF_3C(R^1_aR^2_b)C(R^3_cR^4_d)$, as well as the reaction temperature selected and the yield or conversion desired. For example, typical reaction times for reactions conducted at from about 0° C. to about 65° C., preferably from about 0 to about 25° C., can vary from about 0.1 to about 20 hours; preferably from about 0.1 to about 2.0 hours.

The process described herein is useful for the preparation of fluoroolefins and/or fluorohlaloolefins having the following formula:

$$CF_3CY=CX_nH_p \quad (V)$$

wherein Y is a hydrogen atom or a halogen atom selected from the group consisting of fluorine, chlorine, bromine or iodine; X is a hydrogen atom or a halogen atom selected from the group consisting of fluorine, chlorine, bromine or iodine; n and p are integers independently equal to 0, 1 or 2, provided that (n+p)=2. Such compounds include $CF_3CH=CF_2$, $CF_3CH=CFH$, $CF_3CBr=CF_2$, $CF_3CH=CH_2$, $CF_3CF=CF_2$, $CF_3CCl=CF_2$, $CF_3CH=CHCl$, $CF_3CCl=CHF$, $CF_3CH=CCl_2$, $CF_3CF=CCl_2$, and the like. The fluorine-containing olefins prepared by the method of this invention are readily removed from the reaction mixture and/or solvent or diluent by phase separation. Depending on the extent of conversion of the starting material, the product can be used directly or further purified by standard distillation techniques.

The fluoroolefins obtained by the process of the present invention are useful as monomers for producing fluorine-containing oligomers, homopolymers and copolymers as well as intermediates for other fluorine-containing industrial chemicals.

All references herein to elements or metals belonging to a certain Group refer to the Periodic Table of the Elements as it appears in Hawley's Condensed Chemical Dictionary, 13$^{th}$ Edition. Also, any references to the Group or Groups shall be to the Group or Groups as reflected in this Periodic Table of Elements using the "New Notation" system for numbering groups.

The following examples are given as specific illustrations of the invention. It should be understood, however, that the invention is not limited to the specific details set forth in the examples. All parts and percentages in the examples, as well as in the remainder of the specification, are by weight unless otherwise specified.

Further, any range of numbers recited in the specification or paragraphs hereinafter describing or claiming various aspects of the invention, such as that representing a particular set of properties, units of measure, conditions, physical states or percentages, is intended to literally incorporate expressly herein by reference or otherwise, any number falling within such range, including any subset of numbers or ranges subsumed within any range so recited. The term "about" when used as a modifier for, or in conjunction with, a variable, is intended to convey that the numbers and ranges disclosed herein are flexible and that practice of the present invention by those skilled in the art using temperatures, concentrations, amounts, contents, carbon numbers, and properties that are outside of the range or different from a single value, will achieve the desired result, namely, processes for the preparation of fluoroolefins and reactants used in such processes.

EXAMPLES

Example 1

Dehydrofluorination of $CF_3CH_2CF_2H$ (HFC-245fa)

To 100 mL aqueous solution of KOH (20 wt. %) containing the crown ether, 18-crown-6 (0.050 g, 0.2 mmol), at about 0° C. in an autoclave/pressure bottle was added $CF_3CH_2CF_2H$ (5.93 g, 44 mmol) The stirred reaction mixture was brought to room temperature (about 20–25° C.) gradually and stirred for an additional time period of about 2 hours. The volatile product, $CF_3CH=CFH$, (3.76 g, 33 mmol, 75% yield) formed by the reaction was collected in a cold trap at about −78° C.

Example 2

Dehydrofluorination of $CF_3CH_2CF_2H$ (HFC-245fa)

(A) In the absence of crown ether

To 20 mL aqueous solution of KOH (50 wt. %) at about 0° C. in an autoclave/pressure bottle was added $CF_3CH_2CF_2H$ (6.0 g, 44 mmol). The stirred reaction mixture in the sealed reaction vessel/pressure bottle was brought to room temperature and stirred for 24 hours. Gas chromatographic analysis of the volatile material from the reaction vessel indicated only the unreacted starting material.

(B) In the presence of crown ether

The reaction in (A) was repeated as above except that the crown ether, 18-crown-6, (0.025 g, 0.1 mmol) was added to the reaction mixture. Under these conditions, $CF_3CH=CFH$ (67% yield) (85% conversion) was obtained.

Example 3

Dehydrochlorination of $CF_3CH_2CF_2Cl$ (HCFC-235fa)

To 100 mL aqueous solution of KOH (20 wt. %) containing the crown ether, 18-crown-6, (0.084 g, 0.31 mmol), at about 0° C. in an autoclave/pressure bottle was added $CF_3CH_2CF_2Cl$ (6.4 g, 38.7 mmol). The stirred reaction mixture in the sealed autoclave/pressure bottle was brought to room temperature gradually and stirred additionally for about 1 hour. Gas chromatographic analysis (retention time 1.9 min for $CF_3CH=CF_2$) indicated 93% conversion. The volatile material, $CF_3CH=CF_2$, (3.47 g, 26 mmol, 67% yield) formed during the reaction was collected in a cold trap at about −78° C.

Example 4

Dehydrochlorination of $CF_3CH_2CF_2Cl$ (HCFC-235fa) in the absence of crown ether The reaction of Example 3 was repeated except that the crown ether, 18-crown-6, was not included. Under these conditions, gas chromatographic analysis indicated only the unreacted starting material ($CF_3CH_2CF_2Cl$).

In an effort to drive the dehydrochlorination reaction, more severe conditions were employed. To 100 mL aqueous solution of KOH (20 wt. %) at about 0° C. in an autoclave/pressure bottle was added $CF_3CH_2CF_2Cl$ (8.37 g, 50 mmol). The stirred reaction mixture was heated to and maintained at 65° C. for 2.5 hours. Gas chromatographic analysis indicated 52% conversion to the product. Additional heating for 8 h at 60–65° C. resulted in 93% conversion to product. This indicates that, when the reaction is conducted outside the scope of the present invention, even if dehydrohalogenation occurs, compared with the inventive process, it may require substantially elevated temperature and extended reaction time in order to obtain the product.

Example 5

(A) Preparation of $CF_3CHBrCF_2Br$ Under nitrogen, in to a cooled (−78° C.) 3-necked round bottom flask, equipped with dry ice condenser and stirrer, was added 109 g (0.83 mol) $CF_3CH=CF_2$. Bromine 132 g (0.83 mol) was added drop-wise with stirring over a period of about 4 hours. The temperature during bromine addition ranged from −66 to −46° C. After complete addition, the reaction mixture was stirred for an additional 20 minutes, washed with aqueous sodium bisulfite (10 wt. %) until the organic layer became colorless. The colorless organic layer was separated, dried over $MgSO_4$ and filtered to afford 199 g (82% yield) $CF_3CHBrCF_2Br$ as a colorless liquid. The structure was confirmed by nuclear magnetic resonance (NMR) spectroscopy.

(B) Dehydrobromination of $CF_3CHBrCF_2Br$

To a 250 mL 3-necked round bottom flask operating under nitrogen purge, equipped with a water condenser (at about 15–20° C.), stirrer, and fitted with a dry ice trap (at about −78° C.), was added 100 mL aqueous potassium hydroxide (23 wt. %) solution and the crown ether, 18-crown-6, (0.1 g, 0.37 mmol) To this solution at about 20° C., was added $CF_3CHBrCF_2Br$ (24.6 g, 84 mmol) drop-wise via an addition funnel over a period of about 35 minutes. The dehydrobrominated product, $CF_3CBr=CF_2$ (gas chromatograph retention time, 2.0 min), as formed, was continuously collected in the dry ice trap. After complete addition of $CF_3CHBrCF_2Br$, the reaction mixture was stirred for an additional 60 minutes. A total of 17.1 g (81 mmol) of $CF_3CBr=CF_2$ (96% yield), was collected in the dry ice trap. The structure was confirmed by NMR spectroscopy.

The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art, without departing from the spirit of the invention.

We claim:

1. Process for the preparation of fluorine-containing olefins of the formula $CF_3CY=CX_nH_p$ wherein Y is a hydrogen atom or a halogen atom selected from the group consisting of fluorine, chlorine, bromine or iodine; X is a hydrogen atom or a halogen atom selected from the group consisting of fluorine, chlorine, bromine or iodine; n and p are integers independently equal to 0, 1 or 2, provided that (n+p)=2 comprising contacting, in the presence of a phase transfer catalyst:

(A) a compound of the formula $CF_3C(R^1_aR^2_b)C(R^3_cR^4_d)$, wherein $R^1$, $R^2$, $R^3$, and $R^4$ are independently a hydrogen atom or a halogen selected from the group consisting of fluorine; chlorine, bromine and iodine, provided that at least one of $R^1$, $R^2$, $R^3$, and $R^4$ is halogen and there is at least one hydrogen and one halogen on adjacent carbon atoms; a and b are independently=0, 1 or 2 and (a+b)=2; and c and d are independently=0, 1, 2 or 3 and (c+d)=3;

(B) at least one alkali metal hydroxide;

(C) wherein said process is conducted at from about −5° C. to about 40° C.; and (D) wherein said process is conducted without added solvent or diluent.

2. Process of claim 1 wherein $R^1$ and $R^2$ are hydrogen, $R^3$ is F and c is 2, and $R^4$ is hydrogen or chlorine.

3. Process of claim 2 wherein said phase transfer catalyst is selected from: crown ethers; cryptates; polyalkylene glycols or derivatives thereof; and onium salts.

4. Process of claim 3 wherein said crown ether is selected from 18-crown-6 and 15-crown-5.

5. Process of claim 3 wherein said polyalkylene glycol is selected from polyethylene glycol and polypropylene.

6. Process of claim 3 wherein said onium salt is selected from ammonium and phosphonium-salts.

7. Process of claim 6 wherein said onium salt is selected from the group consisting of benzyltriethylammonium chloride, methyltrioctylammonium chloride, tetra-n-butylammonium chloride, tetra-n-butylammonium bromide, tetra-n-butylphosphonium chloride, bis[tris(dimethylamino) phosphine]iminium chloride and tetratris[tris (dimethylamino)phosphinimino]phosphonium chloride.

8. Process of claim 3 wherein said alkali metal is selected from Group 1 of the Periodic Table of the Elements.

9. Process of claim 3 wherein said alkali metal is selected from lithium, sodium and potassium.

10. Process of claim 9 wherein said alkali metal is sodium and said phase transfer catalyst is 15-crown-5 ether.

11. Process of claim 9 wherein said alkali metal is potassium and said phase transfer catalyst is 18-crown-6 ether.

12. Process of claim 10 wherein said phase transfer catalyst is benzyltriethylammonium chloride.

13. Process of claim 2 wherein the molar ratio of alkali metal hydroxide to $CF_3C(R^1_aR^2_b)C(R^3_cR^4_d)$ is from about 1 to about 10.

14. Process of claim 2 wherein the molar ratio of phase transfer catalyst to $CF_3C(R^1_aR^2_b)C(R^3_cR^4_d)$ is from about 0.001 mol % to abpout 10 mol %.

15. Process of claim 2 wherein $R^4$ is hydrogen.

16. Process of claim 1 wherein $R^1$ is hydrogen and $R^2$ is bromine, $R^3$ is F and c is 2, and $R^4$ is bromine.

17. Process of claim 1 conducted in a continuous manner.

* * * * *